United States Patent [19]

Theisen et al.

[11] 4,418,704

[45] Dec. 6, 1983

[54] INTRAVENOUS PACEMAKER ELECTRODE

[75] Inventors: Peter Theisen; Klaus-Dieter Riechert, both of Berlin, Fed. Rep. of Germany

[73] Assignee: Biotronik Mess- und Therapiegeräte GmbH & Co. Ingenieurbüro Berlin, Berlin, Fed. Rep. of Germany

[21] Appl. No.: 283,477

[22] Filed: Jul. 15, 1981

[51] Int. Cl.³ .............................................. A61N 1/04
[52] U.S. Cl. ................................. 128/785; 128/419 P
[58] Field of Search ............ 128/784, 785, 786, 419 P, 128/642

[56] References Cited

U.S. PATENT DOCUMENTS 3,814,104  6/1974  Irnich et al. ........................ 128/418

Primary Examiner—Kyle L. Howell
Assistant Examiner—Max F. Hindenburg
Attorney, Agent, or Firm—Spencer & Frank

[57] ABSTRACT

A pacemaker electrode has an axially open, hollow cylinder, a plunger axially displaceably received in the cylinder and a securing element for attaching the electrode to the heart. The securing element is mounted on the plunger for movement therewith as a unit. The securing element and the plunger have a withdrawn position in which the securing element is in a substantially fully retracted state within the cylinder. Further, the securing element and the plunger have an advanced position in which the securing element projects from the cylinder. The cylinder has a portion which is substantially pervious to X-rays. The plunger substantially blocks the path of X-rays across the cylinder through the X-ray pervious portion when the plunger and the securing element are in the withdrawn position. The plunger is substantially clear of the X-ray path in the advanced position of the plunger and the securing element, whereby the position of the plunger with respect to the X-ray pervious portion is determinable by an X-ray monitor.

9 Claims, 1 Drawing Figure

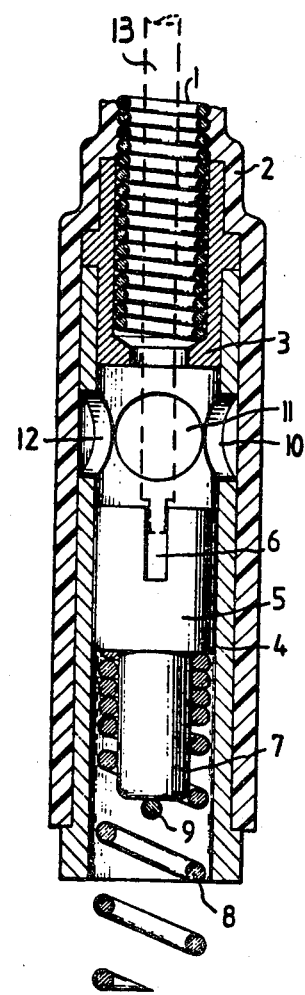

INTRAVENOUS PACEMAKER ELECTRODE

BACKGROUND OF THE INVENTION

This invention relates to an intravenous cardiac pacemaker electrode having a securing element which serves to secure the electrode in the heart and which is mounted on a plunger that is displaceable within a hollow cylindrical. The securing element may be drawn back into the hollow cylinder to assume a protected position for introducing the electrode into the patient.

A pacemaker electrode of the above-outlined type is disclosed, for example, in German Laid-Open Application (Offenlegungsschrift) No. 2,133,304.

An electrode of the above-outlined type has the disadvantage that during its introduction under X-ray monitoring, the implanting surgeons cannot determine from the X-ray image with sufficient clarity whether the securing element is in an extended or in a withdrawn position.

For the purpose of ensuring a complication-free intervention, it is desirable that the implanting surgeon be capable to determine at all times without additional auxiliary means or actions the position of the securing element. This is of particular significance when the electrode has to be removed from an original secured position and has to be displaced to another region of the heart.

A possibility of X-ray monitoring of the implantation of pacemaker electrodes is mentioned in U.S. Pat. No. 3,754,555 in column 2, lines 28–30. It is a disadvantage of the electrode disclosed in this patent as well that the securing element for attaching the electrode in the heart chamber has to be made of a metal which has a predetermined minimum thickness to ensure that it is clearly visible in an X-ray image.

SUMMARY OF THE INVENTION

It is an object of the invention to provide an improved pacemaker electrode of the above-outlined type which is free from the discussed disadvantages and which gives a precise indication of the position of the securing element to the observing physician.

This object and others to become apparent as the specification progresses, are accomplished by the invention, according to which, briefly stated, the hollow cylinder has a wall zone which is substantially transparent (pervious) to X-rays passing transversely through the electrode. When the securing element is in its withdrawn position, the plunger covers the above-noted wall zone, but in an extended position of the securing element, the plunger uncovers such wall zone, so that upon X-ray monitoring the boundary of the wall zone with those cylinder wall zones that have normal thickness (that is, which are not transparent to X-rays) or the boundary of such transparent wall zone with the end of the piston appears clearly on an X-ray monitor.

The invention is based on the recognition that the plunger which, as a rule, is a solid metal body, is the component best able to show its position on the X-ray image by a clearly visible mark. The plunger moves within the hollow cylinder and, preferably in the extended position of the securing element, forms a seal to prevent body liquids from flowing into the inside of the electrode. Due to the fact that the cylinder zones of increased X-ray transparency are situated in the rear zone of the plunger path (relative to the direction of the introduction of the electrode), these zones, when the securing element is in an extended position and thus the plunger is in the forward position, are directly exposed to the substantially laterally impinging X-rays. In such a position the components of the securing element proper also do not block the path of the X-rays. The zones with increased transparency for X-ray irradiation may be constituted by portions of reduced thickness in the wall of the hollow cylinder or by apertures provided therein. A deviation of the shape of the inner side of the hollow cylinder from a geometrical cylindrical shape that would occur necessarily in case apertures are provided, does not constitute a disadvantage as concerns the sealing action of the plunger because such a sealing action needs to be fully effective only when the securing element is in an extended position, that is, the plunger is in an advanced position.

BRIEF DESCRIPTION OF THE DRAWING

The sole FIGURE is an axial sectional view of a preferred embodiment of the invention.

DESCRIPTION OF THE PREFERRED EMBODIMENT

Turning now to the FIGURE, there is shown a helical conductor 1 which is surrounded by a silicone rubber sleeve 2 and which electrically connects the input and the output of a pacemaker (not shown) with the zones of the heart tissue to be stimulated. The helical conductor 1 is illustrated only in part, and the arrangements for an electrical contacting of the pacemaker terminals are not shown for purposes of clarity.

That end of the helical conductor 1 which is adjacent the heart, terminates in a sleeve 3 which, in turn, is surrounded by an end portion of a hollow cylinder 4. The hollow cylinder 4 too, is surrounded along a substantial length by the silicone rubber sleeve 2 which thus electrically insulates from the heart tissue those zones of the electrode that do not contribute to the stimulation or sensing of heart signals.

Within the hollow cylinder 4 there is arranged a longitudinally displaceable plunger 5 which at its rearward zone has a groove 6 engageable by a stylet 13 (shown in phantom lines) provided with a screwdriver-like end. The front face of the plunger 5 carries an axial projection 7 which forms a support for a corkscrew-like helical securing element 8 which serves for immobilizing the electrode in the heart tissue. A transverse pin 9 is secured to the hollow cylinder 4 and projects radially thereinto, between windings of the helical securing screw 8. Thus, when the plunger 5 is rotated by the stylet 13 engaging the groove 6, by virtue of a threading action between the pin 9 and the helical securing screw 8, the latter axially travels into or out of the hollow cylinder 4 by rotation, while, at the same time, the plunger 5 also shifts axially within the hollow cylinder 4.

When that end of the electrode which is adjacent the heart was reached its intended position in which it is to be affixed to the heart, the stylet 13, by means of its screwdriver-like attachment, applies a torque to the plunger 5 and thus the latter and the helical securing element 8 are moved outwardly. During this operation the plunger 5 moves from a position in which it covers apertures 10, 11 and 12 of the hollow cylinder 4 into a position shown in the drawing in which a passage of X-rays through the hollow cylinder 4 oriented substantially laterally is not blocked by the plunger 5. By means of such an arrangement, the implanting physician, upon X-ray monitoring, can follow the position of the plunger 5 and thus the position of the securing screw 8 relative to the hollow cylinder 4 and does not have to rely on other indirect position-determining means, such as feeling the position by the stylet 13 or counting and remembering the number of turns of the stylet 13.

The openings 10, 11 and 12 are so arranged that, in case of substantially laterally penetrating X-rays, independently from the direction of irradiation, the surface zones which are uncovered when the securing element 8 is in its extended position and thus the plunger 5 is in its extended position, become clearly visible in the X-ray image. Preferably, as shown in the drawing, there are provided opening pairs each formed of diametrically aligned openings. As a result, the implanting surgeon can, independently from the axial direction of the electrode, recognize the position of the hollow cylinder 4. Further, in such an arrangement it is not a disadvantage that the X-ray irradiation must penetrate substantially from a lateral direction in order to pass through the openings, since the electrode and, in its position for attachment to the heart chamber, extends substantially parallel to the length dimension of the patient's body, so that it is ensured that the position of the plunger 5 relative to the openings will be clearly visible. Viewing the X-ray screen, the physician will be able to determine the position of the securing element 8 relative to the cylinder 4 either based on the openings (which are circular holes in the embodiment shown) which become visible in the extended position of the piston and their border line with the unweakened portion of the hollow cylinder or based on the boundary of the apertured regions with the rear edge of the piston.

The openings 10, 11 and 12 are so arranged in the illustrated embodiment that, when the securing element 8 is in its extended position, laterally introduced X-rays pass consecutively through two diametrically oppositely located openings (such as, for example, openings 10 and 12). Consequently, the X-rays will be obstructed to a minimum extent. The irradiated openings are in such an arrangement particularly well reproduced on the X-ray screen so that a distinction from the condition where the plunger 5 covers the openings 10, 11 and 12 is very sharp. The apertures 10, 11, 12 are covered by the silicone rubber sleeve 2 to prevent body fluids from entering into the electrode.

In order to ensure that even those X-rays which are at an inclined angle to the radial direction of the hollow cylinder 4 do pass through the openings 10, 11, it is advantageous to so design their dimension in the length of the hollow cylinder 4 that obliquely laterally introduced X-rays can nevertheless pass consecutively through two of the pairwise arranged openings. On the other hand, the dimensions of the apertures should preferably be so selected in the circumferential direction of the cylinder 4 that they are greater than the diameter approx. 1,2 mm of a conventionally used stylet 13, so that even if the stylet 13 is advanced to the groove 6 of the plunger 5, a determination of the position of the helical securing screw 8 is nevertheless easily feasible.

It will be understood that the above description of the present invention is susceptible to various modifications, changes and adaptations, and the same are intended to be comprehended within the meaning and range of equivalents of the appended claims.

What is claimed is:

1. In a pacemaker electrode including an axially open, hollow cylinder having a cylindrical wall; a plunger axially displaceably received in said cylinder and being substantially impervious to X-rays; a securing element for attaching said electrode to the heart; said securing element being mounted on said plunger for movement therewith; said securing element and said plunger having a withdrawn position in which said securing element is in a substantially fully retracted state within said cylinder; said securing element and said plunger having an advanced position in which said securing element projects from said cylinder; the improvement wherein said cylindrical wall comprises a first portion forming a path which is substantially pervious to X-rays and a second portion axially adjoining said first portion and being substantially impervious to X-rays; said plunger substantially blocking said path for X-rays through said first portion in a direction transverse to said cylinder when said plunger and said securing element are in said withdrawn position and said plunger being substantially clear of said path in said advanced position of said plunger and said securing element, whereby the position of said plunger with respect to said first portion being determinable by an X-ray monitor.

2. A pacemaker electrode as defined in claim 1, wherein said first portion is formed of at least one aperture provided in said cylindrical wall.

3. A pacemaker electrode as defined in claim 2, wherein said aperture is covered by an X-ray pervious insulating sleeve surrounding said cylinder.

4. A pacemaker electrode as defined in claim 3, wherein said insulating sleeve is silicone rubber.

5. A pacemaker electrode as defined in claim 1, wherein said first portion comprises a plurality of circumferentially distributed openings for X-rays.

6. A pacemaker electrode as defined in claim 5, wherein said opening form at least one opening pair; the openings of each pair being diametrically arranged in said cylindrical wall.

7. A pacemaker electrode as defined in claim 6, wherein said zones have an elongated configuration in the axial direction of said cylinder.

8. A pacemaker electrode as defined in claim 1, further comprising a stylet introducible axially into said cylinder for manipulating said plunger, and further wherein said first portion has a dimension in the circumferential direction of said cylinder which is greater than the diameter of said stylet.

9. A pacemaker electrode as defined in claim 1, wherein said first portion has an axial dimension permitting the passage of X-rays having an angle of incidence within a range whose limits substantially deviate from the perpendicular with respect to said hollow cylinder.

* * * * *

UNITED STATES PATENT AND TRADEMARK OFFICE
CERTIFICATE OF CORRECTION

PATENT NO. : 4,418,704
DATED : December 6th, 1983
INVENTOR(S) : Peter Theisen et al It is certified that error appears in the above—identified patent and that said Letters Patent is hereby corrected as shown below:

In the heading of the patent, insert --[30] Foreign Application Priority Data  July 16, 1980 [DE] Federal Republic of Germany    3027383--.

Signed and Sealed this

Twenty-seventh Day of March 1984

[SEAL]

Attest:

GERALD J. MOSSINGHOFF

Attesting Officer  Commissioner of Patents and Trademarks